(12) United States Patent
Nakaue

(10) Patent No.: US 12,110,260 B2
(45) Date of Patent: Oct. 8, 2024

(54) PRODUCTION METHOD OF 1,2-DIFLUOROETHYLENE

(71) Applicant: DAIKIN INDUSTRIES, LTD., Osaka (JP)

(72) Inventor: Tsubasa Nakaue, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/294,921

(22) PCT Filed: Nov. 19, 2019

(86) PCT No.: PCT/JP2019/045176
§ 371 (c)(1),
(2) Date: May 18, 2021

(87) PCT Pub. No.: WO2020/105608
PCT Pub. Date: May 28, 2020

(65) Prior Publication Data
US 2022/0017438 A1    Jan. 20, 2022

(30) Foreign Application Priority Data

Nov. 20, 2018   (JP) ................................. 2018-217449

(51) Int. Cl.
   *C07C 17/25*     (2006.01)
   *C07C 17/04*     (2006.01)
   *C07C 17/10*     (2006.01)

(52) U.S. Cl.
CPC ............. *C07C 17/25* (2013.01); *C07C 17/04* (2013.01); *C07C 17/10* (2013.01)

(58) Field of Classification Search
CPC ..................................................... C07C 17/25
See application file for complete search history.

(56) References Cited

U.S. PATENT DOCUMENTS

| | | | | |
|---|---|---|---|---|
| 2,673,884 A * | 3/1954 | Thomas | ............... | C07C 21/18 570/155 |
| 5,118,888 A | 6/1992 | Gervasutti et al. | | |
| 2010/0101953 A1 | 4/2010 | Yokoyama et al. | | |
| 2010/0324345 A1 * | 12/2010 | Bektesevic | ............. | C07C 17/25 570/156 |
| 2013/0035526 A1 * | 2/2013 | Elsheikh | ............... | C07C 21/18 570/155 |
| 2017/0058173 A1 * | 3/2017 | Fukushima | ............... | F25B 1/00 |
| 2017/0253543 A1 * | 9/2017 | Sharratt | ............... | C07C 17/25 |
| 2019/0169101 A1 | 6/2019 | Karube et al. | | |
| 2019/0169102 A1 | 6/2019 | Garrait et al. | | |

FOREIGN PATENT DOCUMENTS

| | | | | |
|---|---|---|---|---|
| FR | 1579576 A | * | 8/1969 | ............. C07C 17/25 |
| GB | 1191192 | | 5/1970 | |
| GB | 2 271 989 | | 5/1994 | |
| JP | 49-11728 | | 3/1974 | |
| JP | 51-13123 | | 4/1976 | |
| JP | 6-219976 | | 8/1994 | |
| JP | 62-30730 | | 8/1994 | |
| JP | 2011-121942 | | 6/2011 | |
| JP | 2013-237624 | | 11/2013 | |
| JP | 2016-124847 | | 7/2016 | |
| JP | 2017-523954 | | 8/2017 | |
| WO | 2005/084794 | | 9/2005 | |
| WO | 2016/016625 | | 2/2016 | |
| WO | 2018/012511 | | 1/2018 | |
| WO | 2018/042114 | | 3/2018 | |

OTHER PUBLICATIONS

PubChem, Source: Ambinter "1-chloro-1,2-difluoroethane", Deposit date May 25, 2018 (Year: 2018).*
Rausch, D. et al. "The addition of fluorine to halogenated olefins by means of metal fluorides" J. Org. Chem., 28, 494-7; 1963 (Year: 1963).*
Patent No. FR1579576A, Aug. 29, 1969, partial machine translation, pp. 1-2 (Year: 1969).*
Hudlický, "Chemistry of Organic Fluorine Compounds", 2nd (Revised Edition) A Laboratory Manual with Comprehensive Literature Coverage, 1992, pp. 491-495.
International Search Report issued Feb. 4, 2020 in International (PCT) Application No. PCT/JP2019/045176.
Nappa et al., "The chlorination of 1, 2-difluoroethane (HFC-152)", Journal of Fluorine Chemistry, 1993, vol. 62, No. 2-3, pp. 111-118.
Extended European Search Report issued Jul. 11, 2022, in corresponding European Patent Application No. 19887701.1.

* cited by examiner

*Primary Examiner* — Medhanit W Bahta
(74) *Attorney, Agent, or Firm* — Wenderoth, Lind & Ponack, L.L.P.

(57) ABSTRACT

Provided is a method for producing 1,2-difluoroethylene, the method being capable of producing 1,2-difluoroethylene with high selectivity. The method for producing 1,2-difluoroethylene according to the present disclosure comprises performing a dehydrochlorination reaction of 1-chloro-1,2-difluoroethane in the presence or absence of a catalyst. The dehydrochlorination reaction is a gas phase reaction or a liquid phase reaction. The production method according to the present disclosure is capable of producing 1,2-difluoroethylene with high selectivity.

3 Claims, No Drawings

PRODUCTION METHOD OF 1,2-DIFLUOROETHYLENE

TECHNICAL FIELD

The present disclosure relates to a method for producing 1,2-difluoroethylene.

BACKGROUND ART

Various methods for producing 1,2-difluoroethylene are known. For example, Patent Literature (PTL) 1 discloses a technique of producing 1,2-difluoroethylene by thermal decomposition of dichlorofluoromethane in the presence of water vapor, followed by hydrogenation of the obtained 1,2-dichloro-1,2-difluoroethylene in the presence of a hydrogenation catalyst.

Further, PTL 2 discloses a technique of producing 1,2-difluoroethylene by a dechlorination reaction or the like of 1,2-difluorotetrachloroethane, followed by hydrogenation and decomposition of the carbon-chlorine bonds in the obtained 1,2-dichlorodifluoroethylene in the presence of a hydrogenation catalyst, such as transition metals.

CITATION LIST

Patent Literature

PTL 1: JP2013-237624A
PTL 2: JPS62-30730A

SUMMARY OF INVENTION

Technical Problem

For conventional methods for producing 1,2-difluoroethylene, however, it is difficult to produce 1,2-difluoroethylene with high selectivity, and its production efficiency is a problem.

The present disclosure has been accomplished in view of the above, and an object of the present disclosure is to provide a method for producing 1,2-difluoroethylene, the method being capable of producing 1,2-difluoroethylene with high selectivity.

Solution to Problem

The present disclosure includes, for example, the subject matter shown in the following items.

Item 1. A method for producing 1,2-difluoroethylene, comprising performing a dehydrochlorination reaction of 1-chloro-1,2-difluoroethane in the presence or absence of a catalyst, wherein the 1,2-difluoroethylene represents only an E-form of 1,2-difluoroethylene, only a Z-form of 1,2-difluoroethylene, or a mixture of an E-form and Z-form of 1,2-difluoroethylene.

Item 2. The production method according to Item 1, wherein the dehydrochlorination reaction is a gas phase reaction.

Item 3. The production method according to Item 1, wherein the dehydrochlorination reaction is a liquid phase reaction.

Item 4. The production method according to Item 3, wherein the dehydrochlorination reaction is performed in an alkaline solution.

Item 5. The production method according to any one of Items 1 to 4, comprising producing the 1-chloro-1,2-difluoroethane by a fluorination reaction of vinyl chloride.

Item 6. The production method according to any one of Items 1 to 4, comprising producing the 1-chloro-1,2-difluoroethane by a chlorination reaction of 1,2-difluoroethane.

Advantageous Effects of Invention

The method for producing 1,2-difluoroethylene according to the present disclosure is capable of producing 1,2-difluoroethylene with high selectivity by a simple method.

DESCRIPTION OF EMBODIMENTS

The present inventors conducted extensive research to solve the problems lying in conventional methods for producing 1,2-difluoroethylene, and found that the above object can be achieved by the use of a dehydrochlorination reaction of 1-chloro-1,2-difluoroethane.

Below, embodiments encompassed by the present disclosure are described in detail. In the present specification, the expressions "comprise" and "contain" encompass the concepts of comprising, containing, consisting essentially of, and consisting of.

The method for producing 1,2-difluoroethylene according to the present disclosure comprises performing a dehydrochlorination reaction of 1-chloro-1,2-difluoroethane in the presence or absence of a catalyst. The dehydrochlorination reaction is in accordance with the following reaction scheme (1):

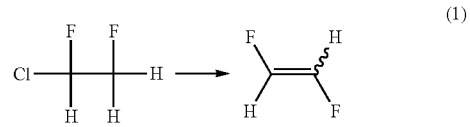

(1)

As shown in reaction scheme (1), in a dehydrochlorination reaction, hydrogen chloride (HCl) is detached from 1-chloro-1,2-difluoroethane (abbreviated below as "HCFC-142a"), thus generating 1,2-difluoroethylene (abbreviated below as "HFC-1132").

HFC-1132 has two different types of isomers, i.e., an E-form and Z-form. 1,2-Difluoroethylene produced by the production method according to the present disclosure represents only the E-form of 1,2-difluoroethylene, only the Z-form of 1,2-difluoroethylene, or a mixture of the E-form and Z-form of 1,2-difluoroethylene. The production method according to the present disclosure usually produces both the E-foam and Z-form. Thus, 1,2-difluoroethylene obtained by the production method according to the present disclosure is usually a mixture of the E-form and Z-form of 1,2-difluoroethylene.

In the present specification, the expression "HFC-1132" refers to the E-form of 1,2-difluoroethylene, the Z-form of 1,2-difluoroethylene, or a mixture of the E-form and Z-form of 1,2-difluoroethylene. Further, in the present specification, only the E-form of 1,2-difluoroethylene is referred to as "HFC-1132(E)," only the Z-form of 1,2-difluoroethylene is referred to as "HFC-1132(Z)," and a mixture of HFC-1132(E) and HFC-1132(Z) is referred to as "HFC-1132(E,Z)," as necessary.

Dehydrochlorination Reaction

The method of dehydrochlorination reaction is not limited. For example, known dehydrochlorination reaction conditions are widely applicable.

The dehydrochlorination reaction may be performed in the absence of a catalyst. Alternatively, the dehydrochlorination reaction may be performed in the presence of a catalyst. To more easily achieve high selectivity of HFC-1132, the dehydrochlorination reaction is preferably performed in the presence of a catalyst.

The type of a catalyst used in the dehydrochlorination reaction is not limited. For example, known catalysts used in a dehydrochlorination reaction may be widely used. Specific examples of catalysts include metal halides; halogenated metal oxides; neutral or zero oxidation state metals or neutral or zero oxidation state metal alloys; activated carbon; chlorine gas; and inorganic absorbents.

When metal halides or halogenated metal oxides are used as a catalyst in the dehydrochlorination reaction, the valence of the metals in these compounds is not limited, and may be monovalent, divalent, or trivalent. It is also possible that multiple metals with different valences be contained. In particular, the metals contained in metal halides or halogenated metal oxides are preferably monovalent or divalent.

The metals contained in metal halides or halogenated metal oxides may be, for example, at least one member selected from the group consisting of Cr, Fe, Mg, Ca, Ni, Zn, Pd, Li, Na, K, and Cs.

The type of halogens contained in metal halides or halogenated metal oxides is not limited, and may be any of F, Cl, Br, and I. Cl is particularly preferred.

Further specific examples of metal halides include LiF, NaF, KF, CsF, $MgF_2$, $CaF_2$, LiCl, NaCl, KCl, and CsCl. To more easily achieve particularly high selectivity of HFC-1132, it is preferable to use one or more members selected from the group consisting of CsCl and $MgF_2$. In particular, it is preferred to use both CsCl and $MgF_2$ in combination. When CsCl and $MgF_2$ are used in combination, the ratio of these is not limited. For example, CsCl may be used in an amount of 1 mass % or more, preferably 2 mass % or more, more preferably 3 mass % or more, and particularly preferably 5 mass % or more, based on the total mass of CsCl and $MgF_2$. Further, CsCl may be used in an amount of 99 mass % or less, preferably 80 mass % or less, more preferably 50 mass % or less, and particularly preferably 30 mass % or less, based on the total mass of CsCl and $MgF_2$.

The method for producing metal halides or halogenated metal oxides is not limited, and a known production method may be used. Metal halides or halogenated metal oxides may also be obtained from, e.g., commercially available products.

When neutral or zero oxidation state metals or metal alloys are used as a catalyst in the dehydrochlorination reaction, for example, it is possible to use one or more members selected from Pd, Pt, Rh, Fe, Co, Ni, Cu, Mo, Cr, and Mn. It is also possible to use an alloy or a mixture containing two or more of these metals. Furthermore, the neutral or zero oxidation state metals or neutral or zero oxidation state metal alloys may be supported on a carrier. The type of carrier in this case is not limited, and known carriers used for supporting a metal are widely applicable.

When activated carbon is used as a catalyst in the dehydrochlorination reaction, its type is also not limited. For example, known activated carbon may be widely used. Activated carbon for use may be in bulk form or may be supported on a carrier. The type of carrier in this case is not limited, and known carriers used for supporting activated carbon are widely applicable.

The method for producing activated carbon is not limited, and for example, a known production method may be used. Activated carbon may also be obtained from, e.g., commercially available products.

When inorganic absorbents are used as a catalyst in the dehydrochlorination reaction, the inorganic absorbents may be an absorbent containing an inorganic compound as a main component. For example, the absorbent is preferably soda lime obtained by using calcium hydroxide as a main component.

The method for producing absorbents is not limited, and for example, a known production method may be used. Absorbents may also be obtained from, e.g., commercially available products.

The catalyst used in the dehydrochlorination reaction is preferably one or more members selected from the group consisting of activated carbon, mixtures of CsCl and $MgF_2$, chlorine gas, and soda lime, to more easily achieve high selectivity of HFC-1132. In particular, to also more easily achieve high conversion of HCFC-142a, the catalyst is preferably one or more members selected from the group consisting of activated carbon, mixtures of CsCl and $MgF_2$, and chlorine gas.

The dehydrochlorination reaction may be a gas phase reaction or a liquid phase reaction. The dehydrochlorination reaction is preferably a gas phase reaction since it is easier to achieve high selectivity of HCFC-142a.

When the dehydrochlorination reaction is a gas phase reaction, the reaction can be performed in the presence of the catalyst mentioned above or in the absence of the catalyst. The reaction is preferably performed in the presence of the catalyst to more easily achieve high selectivity of HFC-1132.

When the dehydrochlorination reaction is a gas phase reaction, for example, dehydrochlorination of HCFC-142a may be performed while introducing HCFC-142a into a reactor in which the reaction is performed from the inlet of the reactor.

When a solid catalyst is used in the gas phase reaction, the dehydrochlorination reaction may be performed by introducing HCFC-142a into a reactor already packed with the catalyst from the inlet of the reactor to bring HCFC-142a into contact with the catalyst. The packed position of the catalyst in the reactor is not limited.

On the other hand, when a gaseous catalyst (e.g., chlorine gas) is used in the gas phase reaction, HCFC-142a may be introduced into a reactor while the gaseous catalyst is introduced into the reactor to bring HCFC-142a into contact with the catalyst. The gaseous catalyst may be introduced from the same inlet as the one into which HCFC-142a is introduced, or from a different inlet. Further, the gaseous catalyst may be introduced from the inlet of the reactor in a mixture state with HCFC-142a.

In the gas phase reaction, the product after the reaction can be collected from the outlet of the reactor, whereby a product containing the target HFC-1132 can be obtained.

In the gas phase reaction of the dehydrochlorination reaction, the flow speed (also called the "flow rate") of HCFC-142a supplied to the reactor is not limited. In the gas phase reaction of the dehydrochlorination reaction, the product containing the target HFC-1132 can be obtained at any flow speed. For example, the flow speed applied to conventional dehydrochlorination reactions is widely applicable.

When the dehydrochlorination reaction is a gas phase reaction in the presence of a solid catalyst, for example, the contact time represented by the ratio ($W/F_0$) of the amount of the catalyst packed in the reactor W(g) to the flow rate of HCFC-142a introduced into the reactor $F_0$ is not limited. In the gas phase reaction of the dehydrochlorination reaction, the product containing the target HFC-1132 can be obtained at any contact time. For example, the contact time applied to conventional dehydrochlorination reactions is widely applicable. Specifically, when the dehydrochlorination reaction is a gas phase reaction in the presence of a solid catalyst, the contact time is preferably 3 to 150 g·sec/mL, more preferably 5 to 145 g·sec/mL, still more preferably 8 to 140 g·sec/mL, and particularly preferably 10 to 135 g·sec/mL.

When the dehydrochlorination reaction is a gas phase reaction in the presence of a gaseous catalyst, the ratio of HCFC-142a and the gaseous catalyst for use is not limited. For example, the gaseous catalyst may be used in an amount of 0.1 to 3 mass %, relative to HCFC-142a.

When the dehydrochlorination reaction is a gas phase reaction, the reaction may be performed either continuously or in batches.

When the dehydrochlorination reaction is a gas phase reaction, the reaction temperature and reaction time of the dehydrochlorination reaction are not limited. For example, in the gas phase reaction, the temperature inside the reactor may be 150° C. or higher and 1500° C. or lower. The temperature inside the reactor is preferably 200° C. or higher, more preferably 250° C. or higher, still more preferably 350° C. or higher, and particularly preferably 400° C. or higher since it is easier to achieve high selectivity of HFC-1132 and high conversion of HCFC-142a. The temperature inside the reactor is preferably 1400° C. or lower, more preferably 1200° C. or lower, still more preferably 1100° C. or lower, and particularly preferably 1000° C. or lower since it is easier to achieve high selectivity of HFC-1132. The reaction time may be set as appropriate according to the reaction temperature.

When the dehydrochlorination reaction is a gas phase reaction, the reaction may be performed either in the presence of an inert gas or in the presence of air. The pressure during the gas phase reaction is also not limited. The reaction may be performed under reduced pressure, increased pressure, or atmospheric pressure.

The dehydrochlorination reaction may also be a liquid phase reaction. When the dehydrochlorination reaction is a liquid phase reaction, the reaction method is not limited. For example, the reaction may be performed under the same conditions as those of known liquid phase reactions.

When the dehydrochlorination reaction is a liquid phase reaction, the dehydrochlorination reaction may be performed in an alkaline solution.

For example, the alkaline solution may be various known alkaline solutions. As the alkali, alkali metal hydroxides, alkaline earth metal hydroxides, various salts of alkali metals, various salts of alkaline earth metals, organic amine salts, ammonium salts, and the like may be widely used. In the alkaline solution, the alkali may be used alone, or in a combination of two or more.

Of these, the alkali is preferably an alkali metal hydroxide. Examples of alkali metal hydroxides include potassium hydroxide and sodium hydroxide.

The solvent in the alkaline solution is not limited. For example, the solvent may be water or an organic solvent. Examples of organic solvents include various solvents capable of forming an alkaline solution, such as alcohol compounds, ketone compounds, ester compounds, and aromatic compounds. Further specific examples of organic solvents include methyl alcohol, ethyl alcohol, acetonitrile, acetone, diglyme, and tetraglyme. Diglyme is preferable since the product can be easily isolated.

The concentration of the alkaline solution is not limited. For example, in the liquid phase reaction, an alkaline solution with an alkali concentration of 1 to 85 mass % may be used.

In the liquid phase reaction, the amounts of HCFC-142a and the alkaline solution for use are not limited. For example, the amount of HCFC-142a for use may be 0.1 to 5 mol, and preferably 0.5 to 1 mol, per mol of the alkali in the alkaline solution.

When the dehydrochlorination reaction is a liquid phase reaction, the liquid phase reaction is preferably performed in the presence of a phase-transfer catalyst. The use of a phase-transfer catalyst allows the reaction to proceed smoothly even when the reaction field is separated into an organic phase and an aqueous phase.

The phase-transfer catalyst is not limited, and known phase-transfer catalysts may be widely used. Specific examples of phase-transfer catalysts include quaternary ammonium salts, such as tetra-n-butyl ammonium salt, tri-n-octyl methyl ammonium salt, and benzyl dimethyl octadecyl ammonium salt; tertiary phosphonium salts, such as tetrabutyl phosphonium salt and benzyl trimethyl phosphonium salt; and macrocyclic polyethers, such as 12-crown-4, 18-crown-6, and benzo-18-crown-6. Of these, tri-n-octyl methyl ammonium chloride (TOMAC) is preferable.

When the dehydrochlorination reaction is a liquid phase reaction, for example, the dehydrochlorination reaction may be performed by placing an alkaline solution and HCFC-142a, and optionally the phase-transfer catalyst mentioned above, in a reactor, followed by mixing.

The reaction temperature in the liquid phase reaction is not limited. For example, in the liquid phase reaction, the temperature inside the reactor may be 30° C. or higher and 300° C. or lower. The temperature inside the reactor is preferably 40° C. or higher, more preferably 50° C. or higher, still more preferably 60° C. or higher, and particularly preferably 70° C. or higher since it is easier to achieve high selectivity of HFC-1132. Further, the temperature inside the reactor is preferably 250° C. or lower, more preferably 200° C. or lower, still more preferably 180° C. or lower, and particularly preferably 150° C. or lower since it is easier to achieve high selectivity of HFC-1132. The reaction time may be set as appropriate according to the reaction temperature.

When the dehydrochlorination reaction is a liquid phase reaction, the reaction may be performed to an extent that the reaction proceeds sufficiently. For example, the reaction may be performed for 1 hour or more and 48 hours or less.

When the dehydrochlorination reaction is a liquid phase reaction, the reaction can be performed in the presence of an inert gas or in the presence of air. The pressure during the liquid phase reaction is also not limited, and the reaction may be performed under reduced pressure, increased pressure, or atmospheric pressure.

In the liquid phase reaction, for example, the product obtained by the dehydrochlorination reaction can be extracted from the gas phase in the reactor. For example, gas is extracted from the gas phase in the reactor and cooled by an appropriate method to liquefy the gas to thus obtain a crude product of the liquid phase reaction. The crude product thus obtained may be heat-treated again at a predetermined temperature, and the gas component vaporized by this heat treatment may be cooled and collected as a liquefied product. The obtained liquefied product may be obtained as a product containing HFC-1132.

Accordingly, in the production method according to the present disclosure, the dehydrochlorination reaction may be performed in either a liquid phase or a gas phase.

In the production method according to the present disclosure, various reactors can be used in the dehydrochlorination reaction. For example, a tubular flow reactor, a pressure-resistant autoclave, or the like can be used as a reactor for the dehydrochlorination reaction. For example, the flow reactor may be an adiabatic reactor, a multitubular reactor in which a heating medium is used to slowly cool the reactor, or the like. The reactor is preferably formed of a material resistant to corrosion, such as stainless steel (SUS). In particular, the reactor is preferably formed of Hastelloy, Inconel, Monel, or the like.

The reactor may also be provided with a jacket for adjusting the temperature inside the reactor. For example, a heat medium or the like may be circulated in the jacket. This makes it possible to adjust the ambient temperature inside the reactor.

In the production method according to the present disclosure, the reaction product obtained by the dehydrochlorination reaction can be optionally purified. The purification method is not limited, and various methods may be used, such as distillation, filtration, liquid separation, and centrifugation.

The reaction product obtained in the dehydrochlorination reaction contains unreacted starting materials, by-products of the dehydrochlorination reaction (e.g., hydrogen chloride), and the like, in addition to HFC-1132, which is the target product.

As stated above, HFC-1132 can have isomers of E-form and Z-form. Thus, in the production method according to the present disclosure, HFC-1132, which is the target product of the production method according to the present disclosure, is HFC-1132(E), HFC-1132(Z), or HFC-1132(E,Z). When HFC-1132 obtained by the production method according to the present disclosure is a mixture of the E-form and Z-form (HFC-1132(E,Z)), the mixing ratio of the E-form and Z-form is not limited, and the E-form and Z-form are included at any ratio.

The production method according to the present disclosure, which comprises performing the dehydrochlorination reaction, is capable of producing HFC-1132 with high selectivity. Additionally, the conversion of HCFC-142a, which is a starting material of the dehydrochlorination reaction, is also high, making it possible to efficiently produce HFC-1132. Further, since the production method according to the present disclosure comprises performing the dehydrochlorination reaction, it is unlikely that a large amount of zinc chloride is undesirably generated as waste as in the technique of PTL 2 stated above.

HFC-1132 obtained by the production method according to the present disclosure can be used for various purposes, including, for example, refrigerants, solvents, and foaming agents. It is also possible to suitably use the HFC-1132 as, for example, a starting material for producing functional materials or functional polymers.

Method for Producing HCFC-142a

In the production method according to the present disclosure, the method for producing HCFC-142a, which is used in the dehydrochlorination reaction, is not limited. For example, known methods may be widely used. Alternatively, HCFC-142a used in the dehydrochlorination reaction may be obtained from, e.g., commercially available products.

For example, HCFC-142a may be produced by a fluorination reaction of vinyl chloride. Alternatively, HCFC-142a may be produced by a chlorination reaction of 1,2-difluoroethane.

Therefore, the production method according to the present disclosure can further comprise producing HCFC-142a by a fluorination reaction of vinyl chloride (which is referred to below as "step a"), or producing HCFC-142a by a chlorination reaction of 1,2-difluoroethane (which is referred to below as "step b"). Steps a and b are performed before the dehydrochlorination reaction.

The method for producing HCFC-142a by a fluorination reaction of vinyl chloride is not limited. For example, known fluorination reaction conditions are widely applicable.

The method for producing HCFC-142a by a chlorination reaction of 1,2-difluoroethane is not limited. For example, known chlorination reaction conditions are widely applicable.

When the production method according to the present disclosure comprises step a or step b, HCFC-142a, which is a starting material of the dehydrochlorination reaction, can be obtained in a high yield. Therefore, the production method according to the present disclosure when comprising step a or b is capable of more efficiently producing HFC-1132.

EXAMPLES

The present disclosure is described in more detail below with reference to Examples. However, the present disclosure is not limited to the embodiments of these Examples.

Example 1

A Hastelloy C reactor with an outer diameter of 1.27 cm, a wall thickness of 0.165 cm, and an inner diameter of 0.94 cm was provided, and nickel mesh (3.0 cm, 9.6 g in total) was placed at the upper part of the reactor to increase the thermal conductivity inside the reactor. The lower part of the reactor was packed with Molsievon X2M activated carbon (3.5 cm, 4.8 g) as a catalyst for a dehydrochlorination reaction. The catalyst was pretreated at 400° C. for 2 hours in the flow of nitrogen gas that had been dried in advance.

The reactor was heated to 250° C., and HCFC-142a was introduced at a rate of 13.4 mL/min (0.06 g/mL), thus performing a dehydrochlorination reaction of HCFC-142a at 250° C. The HCFC-142a was introduced into the reactor so as to flow from the upper part of the reactor to the lower part, and the reaction product was collected from the reactor outlet. The obtained reaction product was supplied to a water washing column to remove HCL and other by-products. Subsequently, the resulting product was allowed to pass through a column packed with a hygroscopic agent to remove the residual moisture content, thus obtaining the target product. Gas chromatography analysis (GC analysis) of the target product revealed that the conversion of HCFC-142a was 5.5 mol %, and the selectivity of HFC-1132 was 99.5 mol %. The obtained HFC-1132 was HFC-1132(E,Z), which is a mixture of the E-form and Z-form.

Example 2

The target product was obtained in the same manner as in Example 1, except that the dehydrochlorination reaction was performed at 450° C. GC analysis of the target product revealed that the conversion of HCFC-142a was 21 mol %, and the selectivity of HFC-1132 was 93.3 mol %. The obtained HFC-1132 was HFC-1132(E,Z), which is a mixture of the E-form and Z-form.

Example 3

The target product was obtained in the same manner as in Example 1, except that the dehydrochlorination reaction was performed at 700° C. GC analysis of the target product revealed that the conversion of HCFC-142a was 89.6 mol %, and the selectivity of HFC-1132 was 90.3 mol %. The obtained HFC-1132 was HFC-1132(E,Z), which is a mixture of the E-form and Z-form.

Example 4

The target product was obtained in the same manner as in Example 1, except that pellets of a mixed catalyst of CsCl and $MgF_2$ (4.0 cm, 7.2 g, mixed mass ratio of CsCl and $MgF_2$:10:90) was used instead of the activated carbon as a dehydrochlorination catalyst, and that the dehydrochlorination reaction was performed at 400° C. GC analysis of the target product revealed that the conversion of HCFC-142a was 2.7 mol %, and the selectivity of HFC-1132 was 99.6 mol %. The obtained HFC-1132 was HFC-1132(E,Z), which is a mixture of the E-form and Z-form.

Example 5

The target product was obtained in the same manner as in Example 4, except that the dehydrochlorination reaction was performed at 450° C. GC analysis of the target product revealed that the conversion of HCFC-142a was 20.6 mol %, and the selectivity of HFC-1132 was 89.3 mol %. The obtained HFC-1132 was HFC-1132(E,Z), which is a mixture of the E-form and Z-form.

Example 6

The target product was obtained in the same manner as in Example 4, except that the dehydrochlorination reaction was performed at 750° C. GC analysis of the target product revealed that the conversion of HCFC-142a was 91.0 mol %, and the selectivity of HFC-1132 was 80.3 mol %. The obtained HFC-1132 was HFC-1132(E,Z), which is a mixture of the E-form and Z-form.

Example 7

A Hastelloy C reactor with an outer diameter of 1.27 cm, a wall thickness of 0.165 cm, and an inner diameter of 0.94 cm was provided. After the reactor was heated to 550° C., a dehydrochlorination reaction of HCFC-142a was performed at 550° C. by introducing, at a rate of 13.4 mL/min (0.06 g/mL), a mixed gas that contains chlorine gas in an amount of 1.5 mass % based on the total mass of HCFC-142a. The reaction product was collected from the reactor outlet, and the reaction product was supplied to a water washing column to remove HCl and other by-products. Subsequently, the resulting product was allowed to pass through a column packed with a hygroscopic agent to remove the residual moisture content, thus obtaining the target product. GC analysis of the target product revealed that the conversion of HCFC-142a was 84.3 mol %, and the selectivity of HFC-1132 was 94.2 mol %. The obtained HFC-1132 was HFC-1132(E,Z), which is a mixture of the E-form and Z-form.

Example 8

The target product was obtained in the same manner as in Example 1, except that soda lime (4.0 cm, 4.1 g) was used instead of the activated carbon as a dehydrochlorination catalyst, and that the dehydrochlorination reaction was performed at 250° C. GC analysis of the target product revealed that the conversion of HCFC-142a was 1.5 mol %, and the selectivity of HFC-1132 was 99.8 mol %. The obtained HFC-1132 was HFC-1132(E,Z), which is a mixture of the E-form and Z-form.

Example 9

The target product was obtained in the same manner as in Example 8, except that the dehydrochlorination reaction was performed at 450° C. GC analysis of the target product revealed that the conversion of HCFC-142a was 19.3 mol %, and the selectivity of HFC-1132 was 98.7 mol %. The obtained HFC-1132 was HFC-1132(E,Z), which is a mixture of the E-form and Z-form.

Example 10

A Hastelloy C reactor with an outer diameter of 1.27 cm, a wall thickness of 0.165 cm, and an inner diameter of 0.94 cm was provided. After the reactor was heated to 715° C., a dehydrochlorination reaction of HCFC-142a was performed at 715° C. by introducing HCFC-142a at a rate of 13.4 mL/min (0.06 g/mL). HCFC-142a was introduced into the reactor so as to flow from the upper part of the reactor to the lower part, and the reaction product was collected from the reactor outlet. The obtained reaction product was supplied to a water washing tower to remove HCl and other by-products. Subsequently, the resulting product was allowed to pass through a column packed with a hygroscopic agent to remove the residual moisture content, thus obtaining the target product. GC analysis of the target product revealed that the conversion of HCFC-142a was 73.1 mol %, and the selectivity of HFC-1132 was 61.8 mol %. The obtained HFC-1132 was HFC-1132(E,Z), which is a mixture of the E-form and Z-form.

Example 11

KOH (35 g, 0.62 mol), water (75 g), tri-n-octyl methyl ammonium chloride (2.0 g, 4.9 mmol), and HCFC-142a (34 g, 0.34 mol) were placed in a 300-mL Hastelloy C autoclave equipped with a cooling tube maintained at 5° C. The reactor was immersed in an oil bath at 120° C., and the mixture was stirred to perform a dehydrochlorination reaction (the temperature of the dehydrochlorination reaction was 120° C.). When the internal pressure of the reactor exceeded 1.5 MPaG (G represents gauge pressure; the same applies below), gas was extracted from the upper part of the cooling tube until the pressure decreased to 1.0 MPaG, and the extracted gas was collected in a cooling trap (−78° C.) connected to the reactor. While repeating this operation, the dehydrochlorination reaction was performed for 20 hours. After the completion of the reaction, the reactor was cooled to 80° C., and the organic substances vaporized at this temperature were all collected in the cooling trap. The reaction product collected in the cooling trap was obtained as the target product. GC analysis of the target product revealed that the conversion of HCFC-142a was 10.5 mol %, and the selectivity of HFC-1132 was 93.5 mol %. The obtained HFC-1132 was HFC-1132(E,Z), which is a mixture of the E-form and Z-form.

The invention claimed is:

1. A method for producing 1,2-difluoroethylene, comprising performing a dehydrochlorination reaction of 1-chloro-1,2-difluoroethane in the presence of a catalyst,
    wherein the 1,2-difluoroethylene represents a mixture of an E-form and Z-form of 1,2-difluoroethylene,
    wherein the dehydrochlorination reaction is a gas phase reaction performed at a reaction temperature of 200-1,000° C.,
    wherein the dehydrochlorination of the 1-chloro-1,2-difluoroethane is performed while introducing the 1-chloro-1,2-difluoroethane from an inlet of a reactor,
    wherein a contact time represented by a ratio $W/F_0$ of the amount of the catalyst packed in the reactor W(g) to a flow rate of the 1-chloro-1,2-difluoroethane introduced into the reactor $F_0$ is 3 to 150 g·sec/mL, and
    wherein the catalyst is soda lime.

2. The production method according to claim 1, comprising producing the 1-chloro-1,2-difluoroethane by a fluorination reaction of vinyl chloride.

3. The production method according to claim 1, comprising producing the 1-chloro-1,2-difluoroethane by a chlorination reaction of 1,2-difluoroethane.

* * * * *